United States Patent [19]
Reinhart

[11] Patent Number: 5,106,838
[45] Date of Patent: Apr. 21, 1992

[54] COSMETIC POWDER COMPOSITIONS

[75] Inventor: Gale Reinhart, Belford, N.J.

[73] Assignee: Revlon, Inc., New York, N.Y.

[21] Appl. No.: 623,002

[22] Filed: Dec. 6, 1990

[51] Int. Cl.$^5$ .......................... A61K 7/42; A61K 47/00
[52] U.S. Cl. ...................................... 514/59; 514/770; 514/785; 514/844
[58] Field of Search ...................... 514/844, 785, 770; 424/59

[56] References Cited
U.S. PATENT DOCUMENTS
4,764,382  8/1988  Kydonieus .......................... 514/509

OTHER PUBLICATIONS

Remington's Pharmaceutical Sciences 15th ed. Mack Pub. Co. Easton, PA 1975.
Cosmetics; Science and Technology 2nd ed. Wiley-Interscience New York, NY 1979.

Primary Examiner—Frederick E. Waddell
Assistant Examiner—Diane Gardner
Attorney, Agent, or Firm—Julie Blackburn

[57] ABSTRACT

The invention is directed to cosmetic powder compositions containing containing esters, a gellant, and polyvinylidene copolymer. These cosmetic compositions are useful for blushes, eyeshadow, and so on.

14 Claims, No Drawings

COSMETIC POWDER COMPOSITIONS

TECHNICAL FIELD

The invention is directed to anhydrous cosmetic compositions containing esters, a gellant, and polyvinylidene copolymer (PVC). These compositions are useful as powders, blushes, eyeshadows, etc.

BACKGROUND OF THE INVENTION

Conventional make-up cosmetics are available in various formulations such as water-based formulations, oil-based formulations, emulsions, and powder formulations. Often, powder formulations are used for cosmetic compositions such as eyeshadow and blush, which are used to apply color to the skin. Many powder formulations are anhydrous systems which contain waxes and oils.

These conventional formulations may be oily and sticky due to the presence of waxes and oils, thus imparting a greasy feel to the skin of the make up wearer. Powder cosmetic formulations containing fat or wax are generally formed by pressing the formulation, or in the alternative, if anhydrous, by heating the ingredients, handling them while they are in the molten state to shape them, then cooling the final product.

Although the presence of waxes in an anhydrous formulation aids in "pourability" in the molding and manufacturing process of the product, these waxes also impart an undesireable greasiness to the final composition. In addition, these steps are time-consuming and costly. There is thus a need for easily molded powder feel cosmetic compositions which do not impart a greasy texture to the final composition.

SUMMARY OF THE INVENTION

The invention is directed to cosmetic compositions comprising 1-50% esters, 3-10% gellant, and 1-15% polyvinylidene copolymer.

The composition contains no wax and is very easily molded during the manufacturing process.

DETAILED DESCRIPTION

The suitable esters in the composition of the invention are derived from carboxylic acids and have the structure RCO—OR' where RCO represents the carboxylic acid radical and where OR is an alcohol residue including but not limited to one or more of octylstearate, isostearyl neopentanoate, octyldodecanol, or polyglycerol 3 diisostearate, or any of the esters set forth on pages 23-25 of the CTFA Cosmetic Ingredient Handbook, First Edition, (1988) which is hereby incorporated by reference. The ester component may comprise only one of the above esters or any mixture thereof. It is preferred to utilize a mixture of esters, most particularly mixtures of octylstearate, isostearyl neopentanoate, octododecanol, and Polyglycerol 3-diisostearate. Most preferred is a cosmetic composition wherein the ester component is 20-40% octylstearate, 5-12% isostearyl neopentanoate, 5-12% octyldodecanol, and optionally, 0.1-5% polyglycerol 3 diisostearate.

The composition of the invention essentially contains 3-10% of a gellant. A gellant is defined as a material which increases the viscosity of nonaqueous products. Suitable gellants, or viscosity increasing agents include ethylene acrylates copolymer (EAC), silica, polyethylene, calcium silicate, ethylcellulose, methoxy PEG-22/Dodecyl Glycol Copolymer, octadecene/maleic anhydride copolymer, polyisobutene, and so on. EAC is preferred. EAC is widely available from a number of commercial sources. The gellant reacts with the ester component to provide a cake which is easily molded, generally eliminating the necessity for waxes.

Finally, the composition essentially contains 1-15% polyvinylidene copolymer. This constituent may be either spherical or nonspherical in shape. The polyvinylidene copolymer may be treated with surface modifiers as is well known in the art. For example polyvinylidene copolymer may be used alone, or it is often combined with talc. Polyvinylidene copolymer may be treated with substances such as isopropyl triisostearyl titanate, lecithin, silicone, teflon, amino acids, sunscreens, polyethylenes, and so on. In the composition of the invention it is preferred that the polyvinylidene copolymer be combined with talc and treated with isopropyl triisostearyl titanate (ITT). These polyvinylidene copolymer products are widely available from a number of commercial sources.

The above three constituents are essential to the composition of the invention. The composition may additionally contain other optional constituents such as emollients, absorbants, fillers, sunscreens, colorants, preservatives, and so on.

It is desireable to add 5-30% of an absorbant. An absorbant is a material which absorbs oil, such as mica, kaolin, sericite, etc. The preferred embodiment contains 5-30% mica.

Suitable emollients include petrolatum, lanolin alcohol, simethicone, lanolins, and those which are not water soluble, listed under the Category "Skin Conditioning Agents—Emollients" on pages 79-80 of the CTFA Cosmetic Ingredient Handbook, First Edition, (1988) which is hereby incorporated by reference. If emollients are added, generally 0.4-16% of the above emollients or mixtures thereof are preferred, and most desireably 4-6% petrolatum, 0.4-0.6% lanolin alcohol, and 0.1-1% simethicone. (The propylene glycol is a carrier for the preservative).

It may also be desireable to add 0.1-30% of one or more powder-type fillers such as silica beads, nylon, talc, color, bismuth oxychloride and so on. The silica may be spherical or nonspherical, untreated, or treated with substances well known in the art and as mentioned above. Nylon may be spherical or nearly spherical in shape. All of the above-mentioned ingredients are widely available from commercial sources. The preferred composition of the invention contains 0.1-15% nylon, 3-10% silica beads, 2-8% talc, and 1-10% titanium dioxide.

It may also be desireable to incorporate into the composition one or more preservatives and colorants. A wide variety of preservatives may be used including but not limited to the parabens, imidiazdidinyl urea, and those set forth under the category "Preservatives" on page 78 of the CTFA Cosmetic Inqredient Handbook, First Edition, (1988) which is hereby incorporated by reference. The preservative is most preferably 0.1-0.3% a mixture of diazolidinyl urea and 0.1-0.3% methyl and propyl paraben.

A wide variety of colorants may be used depending on the color desired for the final composition and its proposed use. Colors include but are not limited to D&C red 6 barium lake, ultramarine blue, black iron oxide, FD&C yellow 5 aluminum lake, yellow iron oxide, red iron oxide, and in addition the colors set forth on page 63 of the CTFA Cosmetic Ingredient Handbook, First Edition, (1988) which is hereby incorporated by reference. Obviously, if the composition of the invention is utilized to make an eyeshadow instead of a blush the color constituents will be different. Generally a preferred range of color is 1-20%.

It may also be very desireable to incorporate sunscreens into the composition of the invention. The sunscreens listed in the CTFA Cosmetic Ingredient Dictionary, First Edition, (1988) which is hereby incorporated by reference, are suitable. Generally 0.1-5% sunscreen is suitable, and the preferred embodiment of the invention contains 0.1-3% octylmethoxycinnamate.

The preferred composition of the invention is as set forth below:

|  | W/W % |
| --- | --- |
| octylstearate | 20-40 |
| polyvinylidene copolymer | 1-10 |
| isostearyl neopentanoate | 5-12 |
| octyldodecanol | 5-12 |
| petrolatum | 4-6 |
| lanolin alcohol | 0.4-1 |
| EAC | 1.6-12 |
| nylon | 0.1-15 |
| mica | 5-30 |
| colors | 1-20 |
| talc | 2-8 |
| silica | 1-10 |
| octylmethoxycinnamate | 0.1-5 |
| polyglycerol 3-diisostearate | 0.1-5 |
| simethicone | 0.1-1 |
| imidazolidinyl urea | 0.1-3 |
| titanium dioxide | 1.0-10 |
| isopropyl triisostearyl titanate | 0.5-2 |
| methyl paraben | 0.1-.25 |
| propyl paraben | 0.1-.25 |
| propylene glycol | 0.1-1 |

The invention will be further described in connection with the following Examples which are set forth for the purposes of illustration only.

EXAMPLE 1

A coral blush was prepared as follows:

|  | W/W % |
| --- | --- |
| octylstearate | 30.00 |
| octylmethoxycinnamate | 2.30 |
| isostearyl neopentanoate | 9.30 |
| octyldodecanol | 6.20 |
| petrolatum | 5.40 |
| lanolin alcohol | 0.60 |
| polyglycerol-3-diisostearate | 0.50 |
| simethicone | 0.30 |
| imidazolidinyl urea | .15 |
| EAC | 10.00 |
| nylon | 10.00 |
| mica | 6.01 |
| polyvinylidene copolymer | 2.50 |
| titanium dioxide | 5.00 |
| D&C Red 6 barium lake | 1.54 |
| ultramarine blue | 0.05 |
| black iron oxide | 0.10 |
| FD&C yellow 5 aluminum lake | 0.50 |
| Yellow iron oxide | 1.20 |
| methyl paraben | 0.20 |
| propyl paraben | 0.15 |
| propylene glycol | 0.50 |
| silica | 3.00 |
| talc | 4.00 |
| isopropyl triisostearyl titanate | 0.50 |

EXAMPLE 2

A peach blush was prepared as follows:

|  | W/W % |
| --- | --- |
| octylmethoxycinnamate | 2.30 |
| octylstearate | 30.00 |
| isostearyl neopentanoate | 9.30 |
| octyldodecanol | 6.20 |
| petrolatum | 5.40 |
| lanolin alcohol | 0.60 |
| polyglyceryl 3 diisostearate | 0.50 |
| simethicone | 0.30 |
| imidazolidinyl urea | 0.15 |
| EAC | 10.00 |
| mica | 6.01 |
| nylon | 10.00 |
| titanium dioxide | 5.00 |
| D&C Red 6 barium lake | 0.60 |
| FD&C yellow 5 aluminum lake | 0.20 |
| black iron oxide | 0.05 |
| yellow iron oxide | 1.82 |
| red iron oxide | 0.72 |
| polyvinylidene copolymer | 7.00 |
| talc | 4.00 |
| isopropyl triisostearyl titanate | 0.50 |
| silica | 3.00 |
| methyl paraben | 0.50 |
| propyl paraben | 0.15 |
| propylene glycol | 0.50 |

EXAMPLE 3

A pink blush was prepared as follows:

|  | W/W % |
| --- | --- |
| octylmethoxycinnamate | 2.30 |
| octylstearate | 26.00 |
| isostearyl neopentanoate | 9.20 |
| octyldodecanol | 5.65 |
| petrolatum | 4.00 |
| lanolin alcohol | 1.00 |
| polyglyceryl-3 diisostearate | 0.50 |
| simethicone | 0.30 |
| imidazolidinyl urea | 1.00 |
| EAC | 2.50 |
| mica | 10.00 |
| nylon | 10.00 |
| propylene glycol | 0.50 |
| titanium dioxide | 10.00 |
| Red 6 barium lake | 3.00 |
| Yellow 5 aluminum lake | 1.20 |
| Ultramarine blue | 0.15 |
| Red iron oxide | 0.10 |
| Polyvinylidene copolymer | 2.3 |
| silica | 10.00 |
| Bismuth oxychloride | 2.00 |
| methyl paraben | 0.20 |
| propyl paraben | 0.15 |

EXAMPLE 4

|  | W/W % |
| --- | --- |
| octylstearate | 25.00 |
| EAC | 8.70 |
| isostearyl neopentanoate | 10.58 |
| octyldodecanol | 5.98 |
| petrolatum | 5.18 |
| lanolin alcohol | 5.00 |
| TiO$_2$/dimethicone | 10.50 |
| Yellow iron oxide dimethicone | 1.50 |
| Red iron oxide/dimethicone | 1.00 |
| mica | 19.31 |
| polyvinylidene copolymer/talc | 7.00 |
| methyl paraben | .15 |

-continued

|  | W/W % |
| --- | --- |
| propyl paraben | .10 |
|  | 100.00 |

The ingredients were combined with heat, and mixed until uniform. The make-up was poured into a pan and allowed to setup.

EXAMPLE 5

|  | W/W % |
| --- | --- |
| octylstearate | 25.00 |
| EAC | 3.70 |
| isostearyl neopentanoate | 9.20 |
| octyldodecanol | 5.20 |
| petrolatum/lanolin alcohol | 4.50 |
| nylon | 10.00 |
| mica | 11.64 |
| Aluminum starch octenylsuccinate | 5.00 |
| TiO$_2$/dimethicone | 13.60 |
| FD&C Yellow 5 Aluminium Lake | 0.30 |
| D&C Red 6 Barium Lake | 0.10 |
| Polyvinylidene copolymer/talc | 7.00 |
| propylene glycol | 0.60 |
| methyl paraben | 0.10 |
| propyl paraben | 0.10 |
| imidazolidinyl urea | 0.20 |
| octylstearate | QS 100.00 |

The above ingredients were mixed with heating until uniform. The make-up was poured into a pan and allowed to setup.

EXAMPLE 6

An eyeshadow composition was made as follows:

|  | W/W % |
| --- | --- |
| petrolatum | 4.32 |
| octylstearate | 27.00 |
| isostearyl neopentanoate | 10.00 |
| octyldodecanol | 5.60 |
| lanolin alcohol | 0.48 |
| propylene glycol | 0.60 |
| methyl paraben | 0.10 |
| propyl paraben | 0.10 |
| Imidazolidinyl urea | 0.20 |
| EAC | 4.70 |
| TiO$_2$ | 6.60 |
| mica | 2.05 |
| Aluminum starch octenylsuccinate | 5.00 |
| Yellow iron oxide | 3.00 |
| Red iron oxide | 1.90 |
| Black iron oxide | 1.35 |
| silica | 4.00 |
| Polyvinylidene copolymer/talc | 7.00 |
|  | 100.00 |

The above ingredients were mixed with heated until uniform. The product was molded into the desired shapes.

While the invention has been described in connection with the preferred embodiment, it is not intended to limit the scope of the invention to the particular form set forth, but, on the contrary, it is intended to cover such alternatives and modifications, and equivalents as may be included within the spirit and scope of the appended claims.

I claim:

1. A waxless cosmetic composition comprising 1-50% of an ester selected from the group consisting of esters derived from carboxylic acids and having the structure RCO-OR' where RCO represents the carboxylic acid radical and where OR' is an alcohol residue, 3-10% of a gellant reactive with said ester, and 5-15% polyvinylidene copolymer.

2. The composition of claim 1 additionally containing an ingredient selected from the group consisting of an emollient, absorbant, filler, sunscreen, colorant, preservative, or mixtures thereof.

3. The composition of claim 2 wherein the esters are selected from the group consisting of more of octylstearate, isostearyl neopentanoate, octyldodecanol, polyglyceryl-3 diisostearate or mixtures thereof.

4. The composition of claim 3 wherein the gellant is selected from the group consisting of ethylene/acrylates copolymer, silica, polyethylene, calcium silicate or mixtures thereof.

5. The composition of claim 4 further comprising 0.4-16% of an emollient.

6. The composition of claim 5 wherein the emollient is selected from the group consisting of petrolatum, lanolin alcohol, simethicone, propylene glycol, or mixtures thereof.

7. The composition of claim 6 further comprising 5-30% of an absorbant.

8. The composition of claim 7 wherein the absorbant is selected from the group consisting of mica, kaolin, sericite, or mixtures thereof.

9. The composition of claim 4 further comprising 0.1-30% filler.

10. The composition of claim 9 wherein the filler is selected from the group consisting of silica beads, nylon, talc, titanium dioxide, bismuth oxychloride, talc, aluminum starch octenylsuccinate, or mixtures thereof.

11. The composition of claim 4 further comprising 0.1-5% sunscreen.

12. The composition of claim 11 wherein the sunscreen is octylmethoxycinnamate.

13. The composition of claim 4 further comprising 1-20% colorant.

14. A cosmetic composition comprising

|  | W/W % |
| --- | --- |
| octylstearate | 20-40 |
| polyvinylidene copolymer | 1-10 |
| isostearyl neopentanoate | 5-12 |
| octyldodecanol | 5-12 |
| petrolatum | 4-6 |
| lanolin alcohol | 0.4-1 |
| EAC | 1.6-12 |
| nylon | 0.1-15 |
| mica | 5-30 |
| colors | 1-20 |
| silica | 1-10 |
| octylmethoxycinnamate | 0.1-5 |
| polyglyceryl-3 diisostearate | 0.1-5 |
| simethicone | 0.1-1 |
| imidiazolidinyl urea | 0.1-3 |
| titanium dioxide | 1.0-10 |
| isopropyl triisostearyl titanate | 0.5-2 |
| methyl paraben | 0.1-0.25 |
| propyl paraben | 0.1-0.25 |
| propylene glycol | 0.1-1.0 |

* * * * *